(12) United States Patent
Amey

(10) Patent No.: US 8,772,546 B2
(45) Date of Patent: Jul. 8, 2014

(54) 1,2-DIAMINOCYCLOHEXANE AND CHEMICAL PROCESS

(75) Inventor: Ronald L. Amey, Wilmington, DE (US)

(73) Assignee: Invista North America S.àr.l., Wilmington, DE (US)

( * ) Notice: Subject to any disclaimer, the term of this patent is extended or adjusted under 35 U.S.C. 154(b) by 757 days.

(21) Appl. No.: 12/612,361

(22) Filed: Nov. 4, 2009

(65) Prior Publication Data

US 2010/0125151 A1 May 20, 2010

Related U.S. Application Data

(60) Provisional application No. 61/115,577, filed on Nov. 18, 2008.

(51) Int. Cl.
*C07C 209/00* (2006.01)

(52) U.S. Cl.
USPC .......................................................... 564/451

(58) Field of Classification Search
None
See application file for complete search history.

(56) References Cited

U.S. PATENT DOCUMENTS

| | | | |
|---|---|---|---|
| 3,308,069 A | 3/1967 | Wadlinger et al. | |
| 3,702,886 A | 11/1972 | Argauer et al. | |
| 3,869,521 A | 3/1975 | Benson | |
| 4,181,680 A | 1/1980 | Butte, Jr. et al. | |
| 4,313,018 A * | 1/1982 | Holy et al. | 585/269 |
| 4,439,409 A | 3/1984 | Puppe et al. | |
| 4,826,667 A | 5/1989 | Zones et al. | |
| 4,954,325 A | 9/1990 | Rubin et al. | |
| 4,960,941 A * | 10/1990 | Vedage et al. | 564/450 |
| 5,149,862 A | 9/1992 | Dorai et al. | |
| 5,236,575 A | 8/1993 | Bennett et al. | |
| 5,250,277 A | 10/1993 | Kresge et al. | |
| 5,360,934 A | 11/1994 | Vedage et al. | |
| 5,362,697 A | 11/1994 | Fung et al. | |
| 5,981,801 A | 11/1999 | Kim et al. | |
| 2010/0125152 A1 * | 5/2010 | Amey | 564/461 |

FOREIGN PATENT DOCUMENTS

JP 59-216852 12/1984

OTHER PUBLICATIONS

JP-59216852 Derwent Abstract, 1994, 3 pages.*
Izvestiya Akademii Nauk SSSR, Seriya Khimicheskaya, 4, pp. 854-857, Apr. 1973.
H. C. Brown and C. A. Brown, JACS, 84, 1494-1495 (1962).

* cited by examiner

*Primary Examiner* — Clinton Brooks
(74) *Attorney, Agent, or Firm* — Robert B. Furr, Jr.

(57) ABSTRACT

Disclosed is a process for the preparation of 1,2-cycloaliphatic diamines from 1,2-aromatic diamines. In one embodiment, the process provides a method for making 1,2-diaminocyclohexane by the reaction of 1,2-phenylenediamine contained in a polar, protic solvent with hydrogen in the presence of a supported rhodium catalyst, ammonia, and an inorganic borohydride, and having enhanced overall conversion and selectivity.

20 Claims, No Drawings

1,2-DIAMINOCYCLOHEXANE AND CHEMICAL PROCESS

CROSS-REFERENCE TO RELATED APPLICATIONS

This application claims the benefit of the filing date of U.S. Provisional Application No. 61/115,577 filed on Nov. 18, 2008, the entire contents of which are incorporated herein by reference.

FIELD OF THE INVENTION

The disclosure herein relates to a process of chemical transformation employing the steps of hydrogenation of 1,2-phenylenediamine (o-phenylenediamine; OPD) to the corresponding cycloaliphatic compound, 1,2-diaminocyclohexane (DCH), by hydrogenating the aromatic diamine in water containing ammonia and an inorganic borohydride in the presence of a supported rhodium catalyst.

BACKGROUND OF THE INVENTION

Litvin and co-workers (Izvestiya Akademii Nauk SSSR, Seriya Khimicheskaya, 4, pp. 854-857, April, 1973) hydrogenated 1,3- and 1,4-phenylenediamine in various solvents at 120° C., 1175 psia, in the presence of supported Ru and Rh catalysts.

U.S. Pat. No. 4,181,680 relates to a process for hydrogenation of an aromatic bis-methylamine at 50° to 150° C., 500 to 2000 psig, in water and the presence of a supported ruthenium catalyst and in the absence of added ammonia.

U.S. Pat. No. 5,360,934 relates to a catalytic hydrogenation process for conversion of aromatic amines to ring hydrogenated compounds in which the catalyst is rhodium on a kappa alumina support.

U.S. Pat. No. 5,981,801 relates to a method for preparation of cycloaliphatic diamines by hydrogenation of the aromatic diamine in the presence of an air or oxygen pre-treated ruthenium catalyst.

JP Patent No. 59216852, May 23, 1983, Nippon Kayaku Co., Ltd. relates to a hydrogenation process for production of aliphatic diamines from the corresponding aromatic diamines by use of a supported rhodium catalyst in water and in the presence of sodium or potassium phosphate and ammonia, a secondary alkylamine, or a tertiary alkylamine.

H. C. Brown and C. A. Brown, JACS, 84, 1494-1495 (1962) disclose the preparation of highly active platinum metal catalysts by the treatment of solutions of platinum metal salts with aqueous sodium borohydride. These catalysts were not prepared on supports such as carbon.

U.S. Pat. No. 3,869,521 claims a catalytic hydrogenation process for conversion of alkylbenzene compounds to the corresponding cyclohexane by using a supported transition metal catalyst prepared by impregnating a support with a solution of a transition metal salt and reducing the transition metal salt in-situ using a sodium borohydride solution.

It would be desirable to provide an improved method for the synthesis of 1,2-diaminocyclohexane that operates at low to moderate pressures to provide commercially useful yield and conversion.

SUMMARY OF THE INVENTION

The invention provides a process for making 1,2-cycloaliphatic diamines comprising contacting a 1,2-aromatic diamine with hydrogen in polar, protic solvent in the presence of an inorganic borohydride, ammonia and a heterogeneous catalyst comprising at least one selected selected from the group consisting of Ru, Rh, Pd and Pt.

In one embodiment, the polar, protic solvents may have the structure ROH where R is hydrogen or an alkyl group. The alkyl group may have from 1 to 6 carbons.

Suitable inorganic borohydrides include alkali metal borohydrides. Examples include sodium borohydride, lithium borohydride, potassium borohydride, and sodium cyanoborohydride. In one embodiment, the inorganic borohydride is sodium borohydride.

In an embodiment, the heterogeneous catalyst comprises at least one selected from the group consisting of Ru and Rh.

In another embodiment, the sum of the weights of Ru, Rh, Pd and Pt comprises from 1 to 10 weight percent of said heterogeneous catalyst, for example, from 3 to 5 weight percent of said heterogeneous catalyst. Suitable catalyst supports include supports known to those skilled in the art of heterogeneous catalysis to be substantially inert to amine solvents. Examples include carbon, alumina and titania. Microporous materials that are substantially inert to amine solvents may also be used. Examples of such materials include zeolites and layered supports.

The heterogeneous catalyst may comprise an oxide of at least one selected from the group consisting of Ru, Rh, Pd and Pt. In this embodiment, the sum of the weights of Ru, Rh, Pd and Pt may comprise more than 50 weight percent of the heterogeneous catalyst, for example 70 or more weight percent. In another embodiment, the heterogeneous catalyst consists essentially of said oxide.

The process of the above embodiments further comprising contacting with hydrogen at a temperature from about 120° to about 200° C., and at a pressure of from about 1000 to about 2500 psig.

In one embodiment, the invention includes a process for making 1,2-diaminocyclohexane comprising contacting 1,2-phenylenediamine contained in a polar, protic solvent with hydrogen in the presence of an inorganic borohydride, ammonia and a supported rhodium catalyst, wherein said polar, protic solvent is selected from the group consisting of water, methanol, ethanol, isopropanol, and mixtures thereof.

Embodiments of the invention include contacting the feed with hydrogen at temperatures from about 120° to about 200° C., and at a gauge pressure of from about 1000 to about 2500 pounds per square inch gauge (psig). [Pressures reported as pounds per square inch gauge (psig) are relative to one atmosphere. 1 pound per square inch=6.895 kilopascal. One atmosphere is equivalent to 101.325 kilopascals, and one atmosphere is about 14.7 pounds per square inch absolute (psia) or about 0 pounds per square inch gauge (psig)].

In one embodiment, the process uses a supported rhodium catalyst. Other useful metal catalysts may include ruthenium. In one embodiment, the rhodium catalyst is supported on carbon and contains from about 1 to about 10 weight percent rhodium. Other useful catalyst supports may include alumina.

In another embodiment, the supported rhodium catalyst may contain from about 3 to about 5 weight percent rhodium.

The disclosures here provide an enhancement to such a process where the overall conversion and selectivity are improved and the process operating pressures are reduced, providing more favorable overall economics.

DETAILED DESCRIPTION OF AN EMBODIMENT

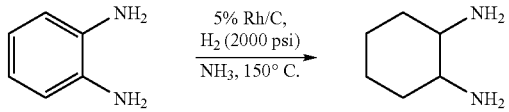

The aromatic diamine starting material is 1,2-phenylenediamine (o-phenylenediamine, OPD).

The hydrogenation process may be carried out in the liquid phase, typically in the presence of a solvent or mixture of solvents. Polar, protic solvents include water, alcohols (methanol, ethanol, isopropanol, etc.), and mixtures thereof. The convenience of using water as the protic solvent for reasons of cost and ease in handling is advantageous.

The hydrogenation may be carried out primarily in stirred, batch, slurry operations at temperatures from about 120° to about 200° C., and at pressures of from about 1000 to about 2500 psig.

Useful catalysts include rhodium supported on alumina, titania, zeolites or carbon, generally containing from about 1 to about 10 weight percent rhodium, for example, from about 3 to about 5 weight percent rhodium. In one embodiment, the support is carbon.

Useful zeolites include those zeolites that are known to those skilled in heterogeneous catalysis to be substantially inert in the presence of amines, inorganic borohydrides or both under reaction conditions for converting 1,2-phenylenediamine to 1,2-diaminocyclohexane. Such reaction conditions may include contact with hydrogen, ammonia, 1,2-phenyldiamine and polar, protic solvents at temperatures from about 120° to about 200° C., and pressure from about 1000 to about 2500 psig.

Natural or synthetic zeolites, a class of aluminum hydrosilicates (also known as crystalline aluminosilicates), having an open structure of three-dimensional networks with defined pores and channels in the crystal, may be used as heterogeneous acid catalysts in the process of the present invention. The particle size of the zeolite may be less than about 0.5 micron, for example less than about 0.1 micron, or less than about 0.05 micron. Examples of useful zeolites include faujasite (described in EP-A 492807), zeolite Y, zeolite Beta (described in U.S. Pat. No. 3,308,069), ZSM-5 (described in U.S. Pat. No. 3,702,886), MCM-22 (described in U.S. Pat. No. 4,954,325), MCM-36 (described in U.S. Pat. No. 5,250,277), MCM-49 (described in U.S. Pat. No. 5,236,575), MCM-56 (described in U.S. Pat. No. 5,362,697), PSH-3 (described in U.S. Pat. No. 4,439,409), SSZ-25 (described in U.S. Pat. No. 4,826,667) and the like.

Other oxides may be useful as catalyst supports provided that they are inert in the presence of amines, inorganic borohydrides or both under reaction conditions as described herein. For example, the preparation of sulfate-doped zirconium dioxide is disclosed in U.S. Pat. No. 5,149,862. Examples of suitable oxidic supports may also include zirconium dioxide, titanium dioxide, hafnium oxide, yttrium oxide, iron (III) oxide, aluminum oxide, tin (IV) oxide, silicon dioxide, zinc oxide or mixture of these oxides.

In one embodiment, both ammonia ($NH_3$) and an inorganic borohydride, for example sodium borohydride, are added to the reaction mixture. The amounts of these constituents may be adjusted with a reasonable amount of trial and error with the objectives of increasing conversion of starting material and improving selectivity to DCH. Ammonia may be added at from about 3 to about 15 molar equivalents relative to the starting o-phenylenediamine (OPD). The inorganic borohydride, (for example: sodium borohydride) may be added at from about 0.02 to about 0.20 molar equivalents relative to the starting OPD.

The reaction mixture may then be worked up according to means known to the skilled person with filtration to remove catalyst, followed by distillation to isolate the refined DCH product.

EXAMPLE

Analysis of reaction products is done using gas chromatography (GC). Examples of suitable GC devices include, for example, the Agilent 6890 N GC (or current equivalent the Agilent 7890A GC system) available from Agilent Technologies, Inc.; Life Sciences and Chemical Analysis Group; 5301 Stevens Creek Boulevard; Santa Clara, Calif. 95051-7201 USA.

In an example, a mixture of 8.0 grams of OPD, 0.2 grams of sodium borohydride, 15 grams ammonia ($NH_3$), 1.6 grams G106 B/W® at 5 wt % Rh carbon powder catalyst from Evonik, Inc., and 60 milliliters of deionized water is loaded into a 300 cubic centimeter volume autoclave, pressurized to 1000 psig with hydrogen at room temperature and then heated for 3 hours at 125° C. to a final pressure of 2000 psig. The reaction products are analyzed by GC. These products are: 83.4 wt % 1,2-diaminocyclohexane (DCH), 2.1 wt % 2-aminocyclohexanol, 8.9 wt % OPD, 1.2 wt % phenazines, 2.0 wt % cyclohexylamine, 0.1 wt % aniline; and 2.0 wt % higher boiling materials.

In a comparative example, a mixture of 8.0 grams of OPD, 30 grams of ammonia, 1.6 grams G106 B/W® at 5 wt % Rh carbon powder catalyst from Evonik, Inc., 0.5 grams of triethylamine, and 60 ml of deionized water is loaded into a 300 cubic centimeter volume autoclave, pressurized to 1000 psig with hydrogen at room temperature and then heated for 4 hours at 150° C. to a final pressure of 2000 psig. The reaction products are removed from the autoclave with dioxane after cooling and analyzed by GC. These products are: 71.4 wt % 1,2-diaminocyclohexane (DCH), 1.0 wt % 2-aminocyclohexanol, 14.8 wt % OPD, 9.8 wt % phenazines, 2.5 wt % cyclohexylamine, and 0.5 wt % aniline.

The foregoing disclosure constitutes a description of specific embodiments illustrating how the invention may be used and applied. Such embodiments are only exemplary. The invention in its broadest aspects is further defined in the claims which follow. These claims and terms used therein are to be taken as variants of the invention described. These claims are not restricted to such variants but are to be read as covering the full scope of the invention implicit within the disclosure herein.

The invention claimed is:

1. A process for making 1,2-cycloaliphatic diamines comprising contacting a 1,2-aromatic diamine with hydrogen in polar, protic solvent in the presence of an inorganic borohydride, ammonia and a heterogeneous catalyst comprising at least one selected from the group consisting of Ru, Rh, Pd and Pt.

2. The process of claim 1 wherein said polar, protic solvent has the structure ROH where R is hydrogen or an alkyl group.

3. The process of claim 2 wherein said alkyl group has from 1 to 6 carbons.

4. The process of claim 1 wherein said inorganic borohydride is an alkali metal borohydride.

5. The process of claim 4 wherein said inorganic borohydride is selected from the group consisting of sodium borohydride, lithium borohydride, potassium borohydride, and sodium cyanoborohydride.

6. The process of claim 5 wherein said inorganic borohydride is sodium borohydride.

7. The process of claim 1 wherein said heterogeneous catalyst comprises at least one selected from the group consisting of Ru and Rh.

8. The process of claim 1 wherein the sum of the weights of Ru, Rh, Pd and Pt comprises from 1 to 10 weight percent of said heterogeneous catalyst.

9. The process of claim 8 wherein the sum of the weights of Ru, Rh, Pd and Pt comprises from 3 to 5 weight percent of said heterogeneous catalyst.

10. The process of claim 1 wherein said heterogeneous catalyst comprises an oxide of at least one selected from the group consisting of Ru, Rh, Pd and Pt.

11. The process of claim 10 wherein said heterogeneous catalyst consists essentially of said oxide.

12. The process of claim 8 wherein said heterogeneous catalyst comprises a support that is substantially inert to amines under reaction conditions for converting 1,2-aromatic diamines to cycloaliphatic diamines.

13. The process of claim 8 wherein said heterogeneous catalyst comprises at least one support selected from the group consisting of alumina, titania, zeolites and microporous layered materials.

14. The process of claim 1 further comprising contacting with hydrogen at a temperature from about 120° to about 200° C., and at a pressure of from about 1000 to about 2500 psig.

15. A process for making 1,2-diaminocyclohexane comprising contacting 1,2-phenylenediamine contained in a polar, protic solvent with hydrogen in the presence of an inorganic borohydride, ammonia and a supported rhodium catalyst, wherein said polar, protic solvent is selected from the group consisting of water, methanol, ethanol, isopropanol, and mixtures thereof.

16. The process of claim 15 further comprising contacting with hydrogen at a temperature from about 120° to about 200° C., and at a pressure of from about 1000 to about 2500 psig.

17. The process of claim 15 wherein said supported rhodium catalyst comprises rhodium on carbon and wherein said supported rhodium catalyst contains from about 1 to about 10 weight percent rhodium.

18. The process of claim 15 wherein said supported rhodium catalyst contains from about 3 to about 5 weight percent rhodium.

19. The process of claim 1, wherein the process is an aqueous process.

20. The process of claim 15, wherein the process is an aqueous process.

* * * * *